(12) United States Patent
De La Cruz et al.

(10) Patent No.: US 11,666,060 B2
(45) Date of Patent: Jun. 6, 2023

(54) ACID WHEY WITH STABLE LACTOSE CONTENT

(71) Applicant: Compagnie Gervais Danone, Paris (FR)

(72) Inventors: Luis De La Cruz, Morristown, NJ (US); Thierry Saint-Denis, Westfield, NJ (US)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 17/023,099

(22) Filed: Sep. 16, 2020

(65) Prior Publication Data

US 2020/0404936 A1 Dec. 31, 2020

Related U.S. Application Data

(63) Continuation of application No. 15/570,975, filed as application No. PCT/EP2016/059843 on May 3, 2016, now abandoned.

(60) Provisional application No. 62/159,423, filed on May 11, 2015, provisional application No. 62/159,425, filed on May 11, 2015, provisional application No. 62/158,386, filed on May 7, 2015, provisional application No. 62/158,390, filed on May 7, 2015.

(51) Int. Cl.

| | |
|---|---|
| *A23C 9/123* | (2006.01) |
| *A23C 9/12* | (2006.01) |
| *A23C 21/00* | (2006.01) |
| *A23C 3/00* | (2006.01) |
| *A23C 21/02* | (2006.01) |
| *C12N 5/00* | (2006.01) |
| *C12P 7/08* | (2006.01) |
| *C12P 19/02* | (2006.01) |
| *C12P 19/04* | (2006.01) |
| *A23C 3/03* | (2006.01) |

(52) U.S. Cl.
CPC ............. *A23C 9/1238* (2013.01); *A23C 3/00* (2013.01); *A23C 3/03* (2013.01); *A23C 9/12* (2013.01); *A23C 9/123* (2013.01); *A23C 21/00* (2013.01); *A23C 21/026* (2013.01); *C12N 5/0018* (2013.01); *C12P 7/08* (2013.01); *C12P 19/02* (2013.01); *C12P 19/04* (2013.01); *A23C 2260/05* (2013.01); *A23Y 2220/15* (2013.01); *A23Y 2240/75* (2013.01); *C12N 2500/84* (2013.01)

(58) Field of Classification Search
CPC ........... A23C 3/00; A23C 3/03; A23C 9/1238; A23C 9/12; A23C 21/00; A23C 9/123; A23C 2260/05; A23C 21/026; A23Y 2220/15; A23Y 2240/75; C12N 5/0018; C12N 2500/84; C12P 7/08; C12P 19/04; C12P 19/02
See application file for complete search history.

(56) References Cited

U.S. PATENT DOCUMENTS

| | | |
|---|---|---|
| 3,818,109 A | 6/1974 | Bechtle |
| 2013/0121976 A1 | 5/2013 | Montserrat et al. |
| 2014/0335226 A1 | 11/2014 | Bell |

FOREIGN PATENT DOCUMENTS

| | | |
|---|---|---|
| WO | 90/05459 A1 | 5/1990 |
| WO | 2013/153414 A1 | 10/2013 |
| WO | 2014/114970 A1 | 7/2014 |

OTHER PUBLICATIONS

Princely et al., Biochemical characterization, partial purification, and production of an intracellular beta-galactosidase from *Streptococcus thermophilus* grown in whey. European Journal of Experimental Biology, 2013, vol. 3(2): 242-251. (Year: 2013).*

Singh RS., Biotechnological Approaches for Valorization of Whey. Advances in Industrial Biotechnology Ram Sarup Singh, Ashok Pandey & Christian Larroche (Eds.) IK International Publishing House Pvt. Ltd., India, Jan. 2014, pp. 443-478 (Year: 2014).*

Wetzel et al., Stress response in Lactococcus lactis and *Streptococcus thermophilus* induced by carbon starvation. Article in Kieler Milchwirtschaftliche Forschungsberichte, Dec. 1999, pp. 1-9. (Year: 1999).*

International Search Report and Written Opinion from International Application No. PCT/EP2016/059843 dated Jul. 20, 2016.

* cited by examiner

*Primary Examiner* — Ganapathirama Raghu
(74) *Attorney, Agent, or Firm* — Greenberg Traurig, LLP

(57) ABSTRACT

The invention relates to improved acid whey compositions, having an improve lactose content and stability. The invention also relates to processes of making such compositions.

7 Claims, No Drawings

ACID WHEY WITH STABLE LACTOSE CONTENT

RELATED APPLICATIONS

This application is a continuation of U.S. patent application Ser. No. 15/570,975, filed Oct. 31, 2017, which is a national phase filing under 35 USC 371 of International Application No. PCT/EP2016/059843, filed on May 3, 2016, which claims priority of U.S. Provisional Application No. 62/158,390, filed on May 7, 2015, U.S. Provisional Application No. 62/158,386, filed May 7, 2015, U.S. Provisional Application No. 62/159,425, filed May 11, 2015, and U.S. Provisional Application No. 62/159,423, filed May 11, 2015, the entirety of which are incorporated herein by reference for all purposes.

The invention relates to improved acid whey compositions, having an improved lactose content and stability. The invention also relates to processes of making such compositions.

Strained fermented dairy products, such as strained yogurts, are products obtained by a process involving a fermentation of a dairy material with lactic acid bacteria, and then a separation step, wherein on one hand a concentrated strained product is obtained, and on another hand an acid whey by product is obtained. As production and consumption of strained products increases, the production of acid whey by-product also increases. The acid whey by-product however finds low usage, and large quantities are to be disposed of, preferably in a nature-friendly fashion, which can require costly treatments. Acid-whey comprises compounds that can be used, such as lactose. Lactose can be for example extracted and used in various applications. Such usage of lactose is however economically challenging: the less lactose the acid whey by-product comprises, the less economically viable the extraction and/or usage thereof is.

Indeed disposal of acid whey is not recommended and lactose valorization thereof is challenging if the lactose content is too low. The lactose content in acid whey has been found to decrease upon storage. Obviating this and maintaining high level of lactose for further valorization can imply significant processing investments and/or operating costs. One solution can be to extract lactose directly after whey separation without transportation to another extraction site having the required equipment. This requires specific investments on the strained fermented product and acid whey by-product production site whereas capacity can be available on other sites. Such a solution lacks flexibility. Another solution can be to freeze the acid whey, to stabilize the lactose content between the recovery (by separation) and the extraction, for example during transportation. Such a solution requires much energy and/or specific transportation equipments. Here also the costs and/or the impacts on nature are not interesting.

There is a need for acid whey compositions with stabilized high lactose contents and/or for useful processes of making the same.

The invention addresses at least one of the needs or problems above with an acid whey composition comprising lactose and lactic acid bacteria, wherein:
the lactose content is of at least 3.20% by weight,
the lactic acid bacteria are at least partly in an alive state,
the lactose stability is of higher than 85%, preferably higher than 88%, during a storage of 7 days at 32° C.

The invention also relates to processes adapted to make the acid whey composition, typically as a by-product of a process of manufacturing strained fermented dairy products. Thus the invention concerns a process comprising the following steps:
a) heat treatment of a dairy material comprising lactose,
b) fermentation with lactic acid bacteria,
c) separation to obtain a strained fermented dairy product and the acid whey composition comprising lactose,
d) optionally smoothing the fermented dairy product,
e) optionally at least one cooling step.

The invention also relates to the uses of the acid whey compositions, such as:
Isolation and purification of lactose to produce crystalline lactose,
Transformation of lactose into glucose, galactose or other sugars through enzymatic treatments,
Transformation of lactose into polysaccharides through enzymatic treatments,
Utilization as a medium to grow biomass with microorganisms, or
Fermentation with yeasts to produce ethanol.

Definitions

The term "acid whey composition" is used herein to describe a by-product of a separation step. The term "acid whey" also encompasses further processed compositions (e.g. filtered acid whey, neutralized acid whey and refined acid whey).

In the present application the lactose metabolization capacity in acid whey refers to the capacity of a lactic acid bacteria to consume lactose in acid whey. The metabolization capacity is typically measured on an acid whey composition having:
from 0.0% to 0.4% by weight of protein,
from 2.8% to 4.7% by weight of lactose,
from 92.0% to 95% by weight of water,
from 0.00% to 0.10% by weight of fat, and
a pH of from 3.80 to 4.65.

The metabolization capacity is preferably determined on an acid whey composition having:
0.4% by weight of protein, preferably of whey protein,
from 2.8% to 4.7% by weight of lactose,
from 94.3% by weight of water,
from 0.0% by weight of fat, and
a pH of 4.5.

In the present application a low lactose metabolization capacity refers to a lactose loss of lower than 15%, preferably lower than 12%, preferably lower than 10%, preferably lower than 8%, preferably lower than 7%, after storage during 7 days at 32° C.

In the present application the lactose stability refers to the lactose conservation, as opposed to the lactose loss, after a storage, preferably of 7 days at 32° C.

Acid Whey Composition

The acid whey composition comprises lactose, in an amount of at least 3.20% by weight, preferably at least 3.50%, preferably at least 4.00%. In one embodiment the acid whey composition comprises at most 6.00% by weight of lactose, for example at most 6.00%.

The lactose stability is of higher than 85%, preferably higher than 88%, preferably higher than 92%, preferably higher than 93%, preferably higher than 94%, preferably higher than 95%, preferably higher than 96%; preferably higher than 97%, preferably higher than 98%; preferably higher than 99%, during a storage of 7 days at 32° C., preferably 7 days from a production at day 0.

The pH of the acid whey composition is preferably of from 3.50 to 4.70.

In one embodiment the acid whey composition has (% by weight):
 from 0.0% to 0.4% of protein,
 from 3.20% to 4.70% of lactose, and
 from 92.0% to 95.0% of water.

The acid whey composition typically comprises water, for example in an amount of higher than 90% by weight. The pH of the acid whey composition can for example be of from 3.50 to 4.70, preferably from 3.80 to 4.65. The acid whey composition is typically substantially free of fat.

The acid whey composition comprises lactic acid bacteria in an alive state. The acid whey composition preferably comprises at least one lactic acid bacteria having a low lactose metabolization capacity in the acid whey, preferably in an alive state.

The acid whey composition can comprise other lactic acid bacteria used for a fermentation step. It is mentioned that the lactic acid bacteria comprised in the acid whey composition are typically alive, particularly the at least one lactic acid bacteria having a low lactose metabolization capacity in the acid whey. Details about bacteria are provided below.

In some embodiments, the acid whey composition is cooled after the separation step. In some embodiments, the acid whey is cooled to a room temperature or below a room temperature. In some embodiment a thermoshocking heat treatment such as a temperature increase is performed between the separation and the cooling.

The acid whey composition is then typically used for lactose recovery (for example extraction by isolation and/or purification) or other applications wherein presence of lactose is valuable.

Preferably the acid whey composition does not undergo a heat treatment step after separation at a temperature that might kill the bacteria comprised therein, for example at a temperature of above 75° C. The process according to the invention allows avoiding such a heat treatment step and thus allows energy savings and/or simplification.

In some embodiments, the process or composition extends the lactose shelf-life in the acid whey by-product by 3 days or more. In some embodiments, the process extends the lactose shelf-life in the acid whey by-product by 7 days or more. In some embodiments, the method extends the lactose shelf-life in the acid whey by-product by 15 days or more. In some embodiments, the process extends the lactose shelf-life in the acid whey by-product by 3 days to 15 days. In some embodiments, the process extends the lactose shelf-life in the acid whey by-product by 3 days to 7 days. In some embodiments, the process extends the lactose shelf-life in the acid whey by-product by 7 days to 15 days. The extension of shelf-life is typically considered with reference to acid whey by-products that do not comprises the at least one lactic acid bacteria that has a low lactose metabolization capacity, in an alive state.

The stabilization of the lactose content of the acid whey by-product (or any carbohydrate derived from it such as glucose or galactose) allows maximizing its value for various applications. Examples valorizations include:
 Isolation and purification of lactose to produce crystalline lactose. Crystalline lactose has value for food applications (such as infant milk formula) and pharmaceutical applications as a filler in various tablet formulations
 Transformation of lactose into other carbohydrates through enzymatic treatments (lactases, invertases) to produce glucose, galactose or other sugar of interest
 Transformation of lactose into polysaccharides such as Galacto-Oligo-Saccharides (GOS) through enzymatic treatment (reverse-lactase), than can be used as a fiber or a functional prebiotic in food applications
 Utilization of the lactose-rich acidic (or neutralized) whey as a medium to grow biomass with micro-organisms of interest, such as yeast, for human or animal nutrition
 Utilization of the lactose-rich whey to grow biomass such as methane-producing micro-organisms for energy production (biodigestion)
 Fermentation with yeasts for example yeast belonging to the genus *Kluyveromyces* that have a unique industrial application as they are capable of fermenting lactose for ethanol production. Surplus lactose from the whey by-product is a potential source of alternative energy.

Lactic Acid Bacteria

The invention involves lactic acid bacteria. Appropriate lactic acid bacteria are known by the one skilled in the art. It is mentioned that lactic acid bacteria are often referred to as ferments or cultures or starters. Examples of lactic acid bacteria that can be used include:
 Lactobacilli, for example *Lactobacillus acidophilus, Lactobacillus casei, Lactobacillus plantarum, Lactobacillus reuteri, Lactobacillus johnsonii, Lactobacillus helveticus, Lactobacillus brevis, Lactobacillus rhamnosus,*
 Streptococci, for example *Streptococcus thermophilus,*
 Bifidobacteria, for example *Bifidobacterium bifidum, Bifidobacterium longum, Bifidobacterium breve, Bifidobacterium animalis,*
 Lactococci, for example *Lactococcus lactis,*
 Propionibacterium such as *Propionibacterium freudenreichii, Propionibacterium freudenreichii* ssp *shermanii, Propionibacterium acidipropionici, Propionibacterium thoenii,*
 mixtures or association thereof.

The lactic acid bacteria preferably comprise, preferably essentially consist of, preferably consist of, *Lactobacillus delbrueckii* ssp. *bulgaricus* (i.e. *Lactobacillus bulgaricus*) and *Streptococcus salivarius* ssp. *thermophilus* (i.e. *Streptococcus thermophilus*) bacteria. The lactic acid bacteria used in the invention typically comprise an association of *Streptococcus thermophilus* and *Lactobacillus bulgaricus* bacteria. This association is known and often referred to as a yogurt symbiosis.

In some particular embodiments the lactic acid bacteria might comprise probiotic bacteria. Probiotic bacteria are known by the one skilled in the art. Examples of probiotic bacteria include some Bifidobacteria and Lactobacilli, such as *Bifidobacterium brevis, Bifidobacterium animalis animalis, Bifidobacterium animalis lactis, Bifidobacterium infantis, Bifidobacterium longum, Lactobacillus helveticus, Lactobacillus casei, Lactobacillus casei paracasei, Lactobacillus acidophilus, Lactobacillus rhamnosus, Lactobacillus plantarum, Lactobacillus reuteri, Lactobacillus delbrueckiisubspbulgaricus, Lactobacillus delbrueckiisubsplactis, Lactobacillus brevis* and *Lactobacillus fermentum.*

In one embodiment the lactic acid bacteria do not comprise Bifidobacteria. In one embodiment the lactic acid bacteria do not comprise *Lactobacillus acidophilus* bacteria. In one embodiment the lactic acid bacteria do not comprise Bifidobacteria and do not comprise *Lactobacillus acidophilus* bacteria.

The lactic acid bacteria can be introduced in any appropriate form, for example in a spray-dried form or in a frozen form. The introduction of the lactic acid bacteria in the dairy material is also referred to as an inoculation.

The invention preferably involves using at least one lactic acid bacteria that has a low lactose metabolization capacity in acid whey, as defined and/or described above. Thus within the lactic acid bacteria mentioned above, at least one bacteria strain is preferably to exhibit a low lactose metabolization in acid whey.

In one embodiment the at least one lactic acid bacteria having a low lactose metabolization capacity in acid comprise a *Lactobacillus bulgaricus* strain. Examples of such *Lactobacillus bulgaricus* strains include *Lactobacillus bulgaricus* strain CNCM I-2787 (deposited according to the Budapest treaty with the *Collection Nationale de Cultures de Microorganismes* as the international depositary authority, on Jan. 24, 2002 under number 1-2787).

In one embodiment the at least one lactic acid bacteria having a low lactose metabolization capacity in acid comprise a *Streptococcus thermophilus* strain. In one embodiment the at least one lactic acid bacteria comprises, preferably essentially consists of, preferably consists of a *Streptococcus thermophilus* strain and a *Lactobacillus bulgaricus* strain. In one embodiment the fermentation step b) is carried out with a culture comprising, preferably essentially consisting of, preferably consisting of, at least one *Streptococcus thermophilus* strain, and at least one *Lactobacillus bulgaricus* strain.

The *Streptococcus thermophilus* bacteria preferably comprise:
  *Streptococcus thermophilus* strain CNCM I-2784 (deposited according to the Budapest treaty with the *Collection Nationale de Cultures de Microorganismes* as the international depositary authority, on Jan. 24, 2002 under number 1-2784),
  *Streptococcus thermophilus* strain CNCM I-2835 (deposited according to the Budapest treaty with the *Collection Nationale de Cultures de Microorganismes* as the international depositary authority, on Apr. 4, 2002 under number 1-2835), and/or
  *Streptococcus thermophilus* strain CNCM I-2773 (deposited according to the Budapest treaty with the *Collection Nationale de Cultures de Microorganismes* as the international depositary authority, on Jan. 24, 2002 under number 1-2773), The *Lactobacillus thermophilus* bacteria preferably comprise:
  *Lactobacillus bulgaricus* strain CNCM I-2787 (deposited according to the Budapest treaty with the *Collection Nationale de Cultures de Microorganismes* as the international depositary authority, on Jan. 24, 2002 under number 1-2787).

Herein, the following references are also used:
  DN-001640 to designate *Streptococcus thermophilus* strain CNCM I-2784,
  DN-001336 to designate *Streptococcus thermophilus* strain CNCM I-2835,
  DN-001236 to designate *Streptococcus thermophilus* strain CNCM I-2773, and
  DN-100290 to designate *Lactobacillus bulgaricus* strain CNCM I-2787.

Process

The acid whey composition can be prepared as a byproduct in a process of manufacturing a strained fermented dairy product from a dairy material. Details of materials and process steps are provided below.

Dairy Material

The process typically involves processing a dairy material. The dairy material is typically comprised of milk and/or ingredients obtained from milk. It is also referred to as a "milk-based composition". Herein milk encompasses animal milk, such as cow's milk, and also substitutes to animal milk, such as vegetal milk, such as soy milk, rice milk, etc.

Milk-based compositions useful in such products and/or processes are known by the one skilled in the art of dairy products, preferably of fermented dairy products. Herein a milk-based composition encompasses a composition with milk or milk fractions, and compositions obtained by mixing several previously separated milk fractions. Some water or some additives can be added to said milk, milk fractions and mixtures. Preferably the milk is an animal milk, for example cow's milk. Some alternative animal milks can be used, such as sheep milk or goat milk.

The milk-based composition can typically comprise ingredients selected from the group consisting of milk, half skimmed milk, skimmed milk, milk powder, skimmed milk powder, milk concentrate, skim milk concentrate, milk proteins, cream, buttermilk and mixtures thereof. Some water or additives can be mixed therewith. Examples of additives that can be added include sugar, sweeteners different from sugar, fibers, and texture modifiers.

The milk-based composition can typically have a fat content of from 0.0% to 5.0% by weight, for example of from 0.0% to 1.0% or from 1.0% to 2.0% or from 2.0% to 3.0% or from 3.0% to 4.0% or from 4.0% to 5.0%. The "fat content" of a composition corresponds to the weight of the fat components present in the composition relatively to the total weight of the composition. The fat content is expressed as a weight percentage. The fat content can be measured by the Weibull-Berntrop gravimetric method described in the standard NF ISO 8262-3. Usually the fat content is known for all the ingredients used to prepare the composition, and the fat content of the product can is calculated from these data.

The milk-based composition can typically have a protein content of from 2.0% to 6.0% by weight, for example of from 2.0% to 3.0% or from 3.0% to 4.0% or from 4.0% to 5.0% or from 5.0% to 6.0%. The "protein content" of a composition corresponds to the weight of the proteins present in the composition relatively to the total weight of the composition. The protein content is expressed as a weight percentage. The protein content can be measured by Kjeldahl analysis (NF EN ISO 8968-1) as the reference method for the determination of the protein content of dairy products based on measurement of total nitrogen. Nitrogen is multiplied by a factor, typically 6.38, to express the results as total protein. The method is described in both AOAC Method 991.20 (1) and international Dairy Federation Standard (IDF) 20B:1993. Usually the total protein content is known for all the ingredients used to prepare the product, and total protein content is calculated from these data.

The dairy material, also referred to as milk-based composition, comprises lactose. The amount of lactose can be typically of from 3.80% to 5.00% by weight.

In one embodiment the dairy material has the following contents (% by weight):
  from 3.0% to 3.5% of milk protein
  from 0.0% to 3.5% of fat
  from 3.80% to 5.00% of lactose.

The pH of the milk can for example be of from 6.60 to 7.00. The dry matter of the milk can be form example of from 6.8% to 13.0%. In one embodiment the milk is a low-fat milk comprising less than 2.0% fat, preferably less than 1.0% fat, preferably less than 0.5% fat. The milk can be for example a skimmed milk.

The ingredients of the milk-based composition and/or the amounts thereof can be selected to have the amounts of proteins and/or fat and/or lactose mentioned above.

Step a)—Heat Treatment

The process typically involves heat treating the dairy material in a step a). Such heat treatments are known by the one skilled in the art, for example as pasteurization or sterilization. They allow eliminating parasite micro-organisms. They can be performed in conventional heat exchangers, such as tubes or plates heat exchangers. The heat treatment can be for example performed at a temperature of from 80° C. to 99° C., preferably 85° C. to 95° C., for example during from 1 minute to 15 minutes.

It is mentioned that the process can comprise a homogenization step before or after the heat treatment step, preferably at a pressure of from 20 bars to 300 bars, in particular from 50 bars to 250 bars.

It is mentioned after the heat treatment the dairy material is typically cooled down to a fermentation temperature.

Step b)—Fermentation

The process typically involves a fermentation step with at least one lactic acid bacteria. In this step the dairy material is inoculated with the lactic acid bacteria, and the mixture is then allowed to ferment at a fermentation temperature. Such inoculation and fermentation operations are known by the one skilled in the art.

During fermentation, the lactic acid bacteria produce lactic acid and thus cause a pH decrease. With the pH decreasing proteins coagulate to form a curd, typically at a breaking pH.

The fermentation temperature can be of from 30° C. to 45° C., preferably from 35° C. to 40° C., with a pH decrease to a breaking pH at which proteins coagulate to form a curd.

The breaking pH is preferably of from 3.50 to 5.50, preferably of from 4.0 to 5.0, preferably from higher than 4.5 to 5.0.

Step c)—Separation

The process typically involves a separation step. In this step the acid whey composition is separated from the curd resulting from the proteins coagulation. Thus one obtains:
- a fermented dairy product, typically comprising the proteins coagulum, referred to a a strained fermented dairy product, and
- the acid whey composition as a by-product.

Such separation steps are known by the one skilled in art, for example in processes of making "greek yogurts". The separation can for example be carried out by reverse osmosis, ultrafiltration, or centrifugal separation. The separation step can be performed for example at a temperature of from 30° C. to 45° C.

The acid whey composition comprises lactose, for example as further described above. In one embodiment an amount of from 65% to 90% by weight, preferably from 70% to 85%, with reference to the amount of dairy material, of acid-whey by-product is recovered.

The strained fermented dairy product comprises a high amount of proteins and is suitable and valuable of consumption. It is also referred to herein as "White Mass".

Step d)—Smoothing

The process of the invention can comprise a step wherein the strained fermented dairy product undergoes a smoothing step. Such steps typically, involving some agitation and/or shear, and are known by the one skilled in the art. The smoothing step can be performed for example by agitation, or by static or dynamic smoothing. In one embodiment the smoothing is a dynamic smoothing, performed with a rotor stator mixer. An example of such an equipment is given in the patent application WO2007/095969. In the context of the invention, "rotor stator mixer" means an equipment in which the product goes through cogged rings, a part of the rings being static, the remaining part being in rotation at a set speed. This system of cogged rings partly static or in rotation applies a defined shearing to the product. Preferably, the rotor stator mixer comprises a ring shaped rotor and a ring shaped stator, each ring of the rotor and the stator being provided with radial slots having a given width, comprising adjusting the rotational speed of the rotor to adjust the peripheral velocity. The rotor may be operated so that the peripheral velocity is between 2 m/s and 13 m/s, in particular between 3 m/s and 5 m/s and more particularly between 3.6 m/s and 4 m/s. For example the process can comprise a dynamic smoothing step, preferably performed with a rotor stator mixer, preferably at a temperature of from 30° C. to 45° C.

Temperatures

In a preferred embodiment:
- the heat treatment step a) is performed at a temperature of from 80° C. to 99° C., preferably 85° C. to 95° C.,
- the fermentation step b) is performed at a temperature of from 30° C. to 45° C., and or
- the separation step is performed at a temperature of from 30° C. to 45° C.

It is mentioned that the process can comprise at least one cooling step. For example the process can involve a cooling between the heat treatment step and the fermentation step. The process can involve a cooling step performed on the strained fermented dairy product, to reach a storage temperature, for example a chilled temperature of from 1° C. to 10° C., for example 4° C. The process can involve a cooling step performed on acid whey by-product, to reach a storage temperature, for example a room temperature. In one embodiment the process comprises a cooling step e1) of the fermented dairy product, to a temperature of from 4° C. to 10° C. In one embodiment the process comprises a cooling step e2) of the acid whey by-product to a room temperature, preferably to from 15° C. to 25° C.

In a preferred embodiment the process of the invention comprises a heat treatment step such as a temperature increase step, at the end of the fermentation and before the separation, referred to as thermoshocking step. This step is typically performed by raising the temperature to a temperature from 50° C. to 75° C., preferably from 50° C. to 60° C. Such a thermoshocking step can contribute to stabilizing the organoleptic properties of the strained dairy fermented product. Alternatively, a heat treatment can be performed after the separation step on the acid whey composition with similar increase in temperature. It is believed that at least a part of the lactic acid bacteria remains alive after such a treatment. It has been surprisingly found that such a thermoshocking step can increase the stabilization of the amount of lactose in the acid whey composition.

In one preferred embodiment the process involves the following phases: Fermentation→Temperature increase (Thermoshocking)→Separation→cooling of strained fermented dairy product and of acid whey by-product.

In one preferred embodiment the process involves the following phases: Fermentation→Separation→Cooling of strained fermented dairy product and temperature increase (Thermoshocking) of acid whey by-product→cooling of acid whey by-product.

These embodiments are found to be efficient from an energy management point of view as allowing an increase of temperature (Thermoshocking) from a fermentation or separation temperature typically of from 30° C. to 45° C. to a temperature of from 50° C. to 75° C. Such embodiments consume less heating and/or cooling energy than embodiment wherein the acid whey by-product would be cooled and then significantly heat-treated for example at a pasteurization or sterilization temperature.

Further details or advantages of the invention might appear in the following non limitative examples.

EXAMPLES

Example 1—Manufacture of Strained Fermented Dairy Products and Acid Whey by-Products Strained fermented dairy products are manufactured at pilot scale with using the following ingredients:
  Milk: Skimmed milk having 3.17% protein, 0% fat and 8.8% dry matter
  Cultures:
  Culture 1: Yo-Mix® 495, marketed by Dupont
  Culture 2: Mixture of the following bacterial strains: *Streptococcus thermophilus* DN-001640, *Streptococcus thermophilus* DN-001336, *Streptococcus thermophilus* DN-001236, and *Lactobacillus bulgaricus* DN-100290.
The procedure involves the following steps:
  heat treatment of milk at a temperature of 95° C. during 6.5 minutes,
  homogenization at a temperature of 60° C., at a pressure of 69 bars,
  inoculation of milk at 40° C. with 0.02% by weight of culture,
  fermentation at a temperature of 40° C. to reach a breaking pH of 4.65,
  optionally: temperature increase ("fermented mix thermoshock") to a temperature of 59.5° C. during 2.5 minutes,
  separation, at a temperature of 41.5° C., of 72% of whey, with a Westphalia KNA3 pilot scale centrifuge separator, to obtain:
  A) a strained fermented dairy product, and
  B) an acid whey by-product, and
  dynamic smoothing, performed on the strained fermented dairy product.

Example 2—Acid-Whey

The acid whey is collected as aliquot to sterile specimen cups. Separate samples are collected:
  A "reference" sample which is aliquot and immediately frozen by placing it in a chamber to stop any lactose metabolization,
  A "32° C. storage" sample which is aliquot and placed in a 32° C. chamber,
  A "4° C. storage" sample which is aliquot and placed in a 4° C. chamber,
  An "Acid whey thermoshock" sample which is heat treated at 58° C. during 2.5 minutes using a metal beaker and a hot plate, and then aliquot and placed in a 4° C. chamber.
All acid whey samples are kept in their respective chambers for 7 days before they are frozen in the −4° C. chamber and then analyzed within 24 hours of chamber transfer.
Acid Whey Analysis
The lactose content and *Streptococcus* bacteria populations are analyzed (National Food Lab, Livermore, Calif.).
Lactose analysis results are reported on tables 1 and 2 below:
  Remaining lactose in the acid whey (g of lactose per 100 g of acid whey)
  *Steptococcus thermophilus* count (CFU per g)
  Lactose loss, compared to the "reference" sample:

$$\text{Lactose loss} = (\text{sample value} - \text{reference reference})/\text{reference value}$$

Here a negative value indicates a loss.

TABLE 1

|  | Culture 1 | Culture 2 |
|---|---|---|
| "32° C. Storage" Remaining lactose (%) | 3.16 | 3.87 |
| "32° C. Storage" Lactose loss | −22% | −6.5% |
| "Acid whey thermoshock" Lactose loss | <−2% | −1.0% |

This shows that Culture 2 allows higher conservation of lactose in acid whey.

TABLE 2

|  |  | Remaining lactose (%) | S. thermophilus (CFU/g) | Lactose Loss |
|---|---|---|---|---|
| Culture 1 | 4° C. Storage | 3.81 | 6.0 × 10^7 | −6% |
|  | 32° C. Storage | 3.16 | 9.6 × 10^6 | −22% |
| Culture 2* | Acid whey thermoshock | 3.98 | 6.9 × 10^7 | −1.0% |
|  | 4° C. Storage | 3.87 | 1.4 × 10^8 | −3.5% |
|  | 32° C. Storage | 3.76 | 8.0 × 10^3 | −6.5% |

*average on 2 productions

As there is a CFU count (Colony Forming Units) is shows that at least part of the lactic acid bacteria are alive, even after a thermoshock treatment. As the lactose loss is reduced with this treatment, it suggests that this treatment places the bacteria into an alive form with reduced lactose metabolism.

Under 32° C. chamber conditions, the highest level of biomass available is found with Culture 2. Interestingly and surprisingly, Culture 2 also has the lowest level of lactose at those conditions which means a lesser amount of biomass is needed to consume lactose. This shows that a culture selection can play a role in the stabilization of lactose in the acid whey.

Example 3—Strained Fermented Dairy Product

The strained fermented dairy products, also referred to as "White Mass" (WM), are processed as finished products. For plain products 6 oz of White Mass are conditioned in cups.

For Strawberry Fruit On the Bottom (FOB) products, 2 oz (25%) of a strawberry preparation and then 4 oz (75%) of White Mass are dosed in a cup.

The products obtained with Culture 1 and with Culture 2 are compared for overall balance by a trained panel, at D28 (28 days of storage at 4° C. after preparation) and D55 (55 days of storage at 4° C. after preparation). Most significant and important differences in attributes are reported on table 3 below.

Overall balance attributes: Evaluation of the roundness of flavor, of the lack of spike from any tastes or flavor, and of the lack of overpowering notes

TABLE 3

| | Culture 2, with reference to Culture 1 |
|---|---|
| Plain Product D28 | More overall balance (score difference 0.6) |
| Plain Product D55 | More overall balance (score difference 0.8) |
| Strawberry FOB Product D28 (stirred before tasting) | More overall balance (score difference 0.6) |
| Strawberry FOB Product D55 (stirred before tasting) | More overall balance (score difference 0.6) |

These results show that the products obtained with Culture 2 have an improved overall balance, and that the difference is even higher for the White Mass part after an extended shelf-life of 55 days.

Example 4—Post-Acidification

The post-acidification of the white mass is evaluated by pH measurements at DO (after preparation), and D7 (7 days of storage at 4° C. after preparation). The results are reported on table 4 below.

TABLE 4

| | Plain Product with Culture 1 | Plain Product with Culture 2 |
|---|---|---|
| pH at D 0 | 4.50 | 4.45 |
| pH at D 7 | 4.45 | 4.40 |
| Loss of pH from D 0 to D 7 | −1.1% | −1.1% |

This shows that the post-acidification of the strained fermented dairy product is similar with Culture 1 (pH drop of 1.1%) and Culture 2 (pH drop of 1.1%). However, surprisingly, the lactose stability in the corresponding acid whey by-products it very different with Culture 1 (lactose loss of 22%) and Culture 2 (lactose loss of 6.5%), as shown on table 1 and table 2. This shows that the lactose metabolization capacity of the cultures in acid whey is not directly correlated to post-acidification capacity in the strained fermented dairy product.

The invention claimed is:

1. A method for manufacturing an acid whey composition, comprising:
   a) heating a dairy material comprising lactose,
   b) fermenting the dairy material with lactic acid bacteria, wherein the fermentation step b) is performed with a mixed culture comprising *Streptococcus thermophilus* strain CNCM I-2784, strain CNCM I-2835, strain CNCM I-2773, and *Lactobacillus bulgaricus* strain CNCM I-2787,
   c) separating the dairy material to obtain a strained fermented dairy product and the acid whey composition,
      wherein the acid whey composition comprises lactose and lactic acid bacteria,
         wherein the lactose content is of at least 3.20% by weight,
         wherein the lactose has a stability of higher than 85% during a storage of 7 days at 32° C.,
         wherein at least a portion of the lactic acid bacteria is in an alive state,
         wherein the lactic acid bacteria has a lactose metabolization capacity of lactose loss of lower than 15% after storage for 7 days at 32° C., and
   d) stabilizing the lactose of the acid whey composition, wherein step d) comprises one of:
      i) isolating and purifying the lactose of the acid whey composition to produce crystalline lactose,
      ii) enzymatically treating the lactose of the acid whey composition resulting in glucose, galactose or other sugars, or
      iii) enzymatically treating the lactose of the acid whey composition resulting in polysaccharides.

2. The method according to claim 1, further comprising a homogenization step before or after the heating step a).

3. The method according to claim 1, wherein at step c) an amount of 10% to 30% by weight, with reference to the amount of dairy material, of acid-whey composition is recovered.

4. The method according to claim 1, further comprising at least one cooling step, wherein the at least one cooling step comprises:
   e1) cooling the fermented dairy product, or
   e2) cooling the acid whey composition.

5. The method according to claim 4, wherein said cooling step of e2) is performed at a temperature of 15° C. to 25° C.

6. The method according to claim 1, further comprising performing a thermoshocking heat treatment step at a temperature of 50° C. to 75° C.:
   between the fermentation step b) and the separation step c), or
   after the separation step c), on the acid whey composition.

7. The method according to claim 6, wherein the thermoshocking heat treatment step is performed at a temperature of 50° C. to 60° C.

* * * * *